United States Patent [19]

Arner et al.

[11] Patent Number: 4,566,293
[45] Date of Patent: Jan. 28, 1986

[54] METHOD OF SAMPLE PREPARATION AND APPARATUS THEREFOR

[75] Inventors: Russell E. Arner, Brunswick; Ronald J. Emrich, Shaker Heights; James Gianelos, Lyndhurst; Marlon L. Haynes, Stow, all of Ohio

[73] Assignee: The B. F. Goodrich Company, Akron, Ohio

[21] Appl. No.: 677,252

[22] Filed: Dec. 3, 1984

[51] Int. Cl.[4] .................................... F25B 19/00
[52] U.S. Cl. .................................. 62/514 R; 62/331; 98/115.3; 128/1 B; 422/104
[58] Field of Search ..................... 62/514 R, 331; 98/115.3; 128/1 B; 422/104

[56] References Cited

U.S. PATENT DOCUMENTS

| | | | |
|---|---|---|---|
| 3,907,389 | 2/1975 | Cox et al. | 128/1 B |
| 4,059,903 | 11/1977 | Piet et al. | 98/115.3 |
| 4,324,285 | 4/1982 | Henderson | 62/514 R |
| 4,356,967 | 11/1982 | Lunick | 128/1 B |

Primary Examiner—Ronald C. Capossela
Attorney, Agent, or Firm—James R. Lindsay

[57] ABSTRACT

A process and apparatus are provided that permits a sample to be cooled below the glass transition temperatures of the components of the sample without forming objectionable frost on the surface of the sample. In accordance with the invention, the sample is confined within a freeze box that is hermetically-sealed from the ambient atmosphere. The freeze box is purged with a dry inert gas until essentially all moisture is removed from the freeze box. The sample then is rapidly cooled to a temperature below the glass transition temperature of the components of the sample before being transferred to an analysis instrument without exposing the sample to ambient atmosphere.

4 Claims, 6 Drawing Figures

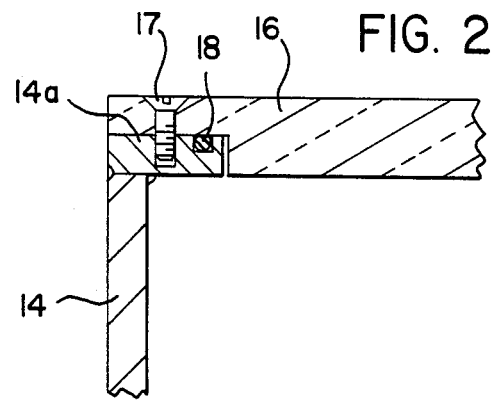
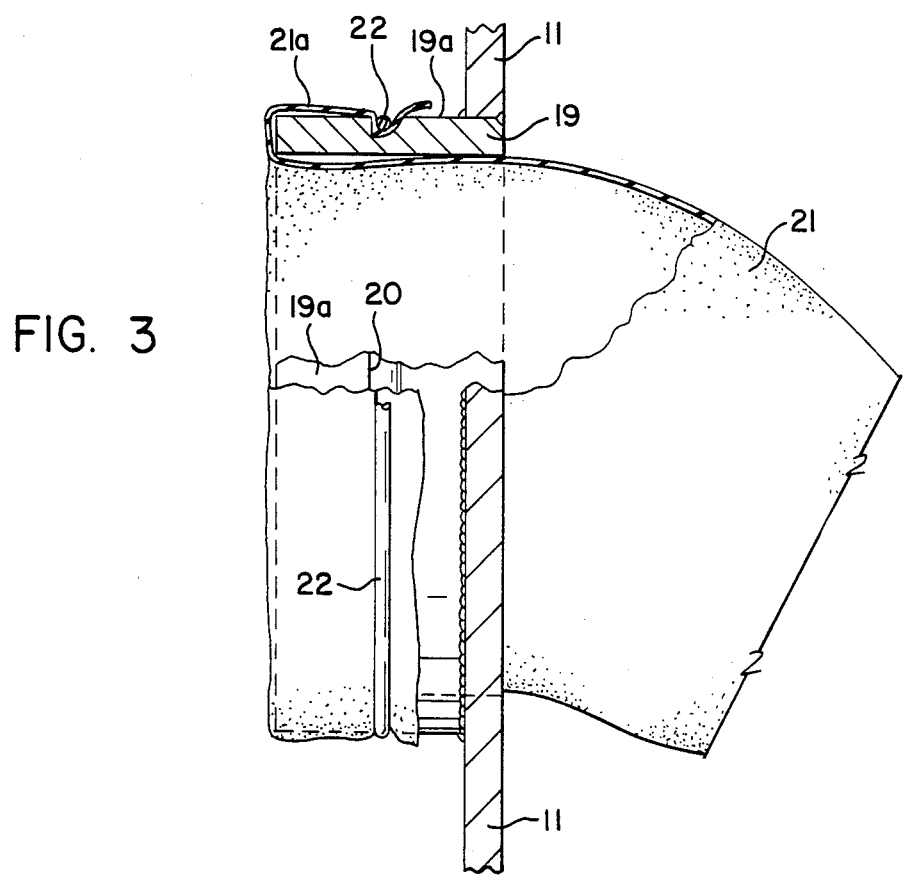

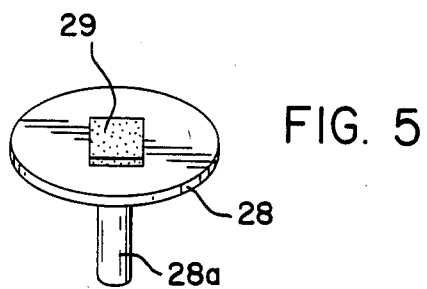
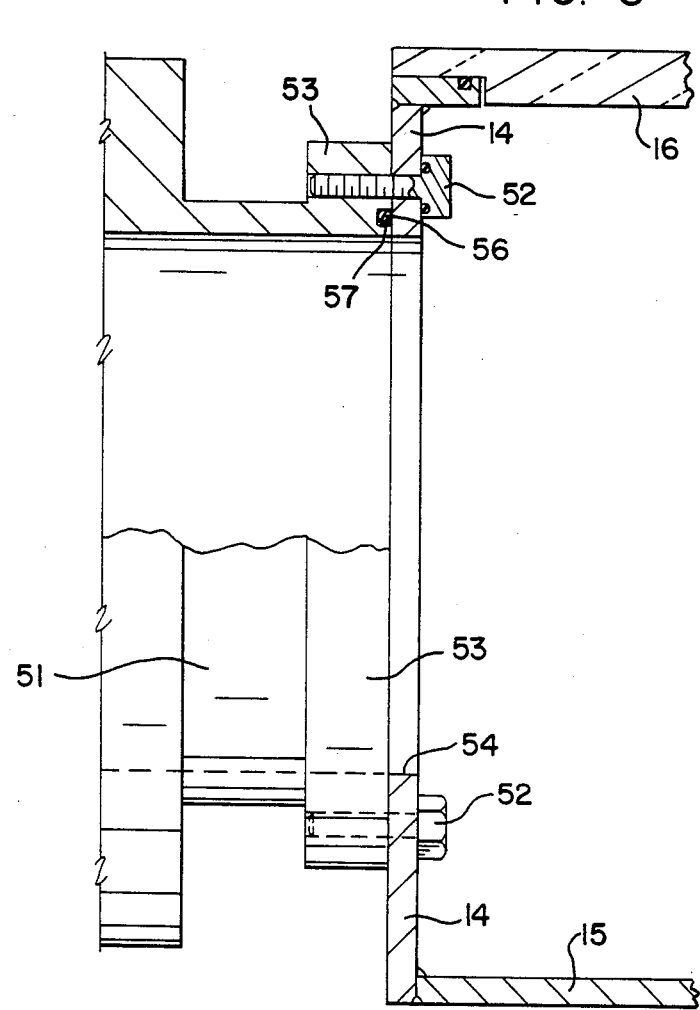

METHOD OF SAMPLE PREPARATION AND APPARATUS THEREFOR

BACKGROUND OF THE INVENTION

The present invention pertains to a method for preparing a sample for surface analysis in ultrahigh vacuum surface analysis instruments and to apparatus for accomplishing such preparation.

In the scientific community, as well as in industry, it often is desirable to obtain a chemical or physical analysis of the surface of a sample of material. Various surface analysis instruments have been developed which employ a high vacuum environment in which the sample remains during the analysis. One such surface analysis instrument is known as the VG Escalab MKII sold through VG Instruments Inc., Stamford, Conn.

Many materials desired to be surface-analyzed at ambient temperatures are liquid or, when solid, contain components which are liquids (for example, oils, compounded plastics and rubbers, latices, biological samples, etc.). If samples of such materials are subjected to a high vacuum at ambient temperature, the liquid materials in practically all instances will flash vaporize with resultant massive instant contamination of the analysis system, while any liquid components contained in a multi-component, apparently solid, material would diffuse to the surface of the sample to produce erroneous surface analysis results and ultimately outgas into the vacuum environment with resultant contamination of the analysis system. The only practical way of preventing the aforesaid difficulties is to immobilize any potentially mobile material in the sample. One way of accomplishing this desired result would be to reduce the temperature of the sample to a temperature below the glass transition temperature (Tg) of all of the substances contained in the sample to be surfaced-analyzed, desirably to a temperature of $-110°$ C. or lower. Such reduction in temperature must be done before the sample is exposed to the high vacuum at which the surface-analysis will be performed. However, if the temperature of a sample is reduced sufficiently to immobilize its component materials in a normal atmosphere, moisture in the atmosphere will condense as frost on the surface of the sample. Introduction of the frost covered sample into a high vacuum environment of the surface analysis instrument, even if such environment also is cooled to a temperature at which the components of the sample are immobilized, will not permit a proper analysis of the surface of the sample material, since the analysis will only indicate the presence of a water surface layer (i.e., the frost deposit). In order to avoid the formation of frost on the surface of a sample to be surface-analyzed in a high vacuum environment, the atmosphere surrounding the sample must contain under 0.1 part per million (ppm) of water in the form of moisture (desirably below 0.01 ppm of water) when the temperature of the sample is lowered. Since it is not possible to remove all moisture from an atmosphere, it also is important to cool the sample to the desired temperature (desirably to $-110°$ C. or below) as quickly as possible (desirably within 10 to 15 minutes) and then to admit the sample immediately into the high vacuum surface analysis instrument for analysis. Equipment which presently is available has not been found to be able to cool a sample of material containing volatiles to the desired low temperature before the sample's introduction into the high vacuum environment for surface analysis without the formation of objectionable frost on the surface of the sample.

SUMMARY OF THE INVENTION

The present invention provides a process and apparatus that permits a sample desired to be surface-analyzed under a high vacuum-cold environment to be cooled below the glass transition temperatures of the components of the material to be surface-analyzed without the formation of objectionable frost on the surface of the sample. In accordance with the present invention, the sample to be analyzed is placed within a freeze box that is hermatically sealed from the ambient atmosphere, after which the environment within the freeze box is flushed with extremely dry nitrogen gas to reduce the moisture content within the freeze box to below 0.1 ppm of water. The sample to be analyzed then is cooled rapidly to a temperature below the glass transition temperature of the various components contained in the sample and immediately after being cooled is introduced into the high vacuum chamber in which the surface of the sample is to be analyzed in the customary manner.

DESCRIPTION OF THE DRAWINGS

FIG. 2 is a section view along line 2—2 of FIG. 1;

FIG. 3 is a section view along line 3—3 showing an air-impervious glove assembled on a glove mounting ring of the freeze box shown in FIG. 1;

FIG. 5 is a perspective view of a sample holder with a sample positioned thereon; and FIG. 6 is a section view along line 6—6 of FIG. 1.

DETAILED DESCRIPTION OF THE INVENTION

Figure 1:
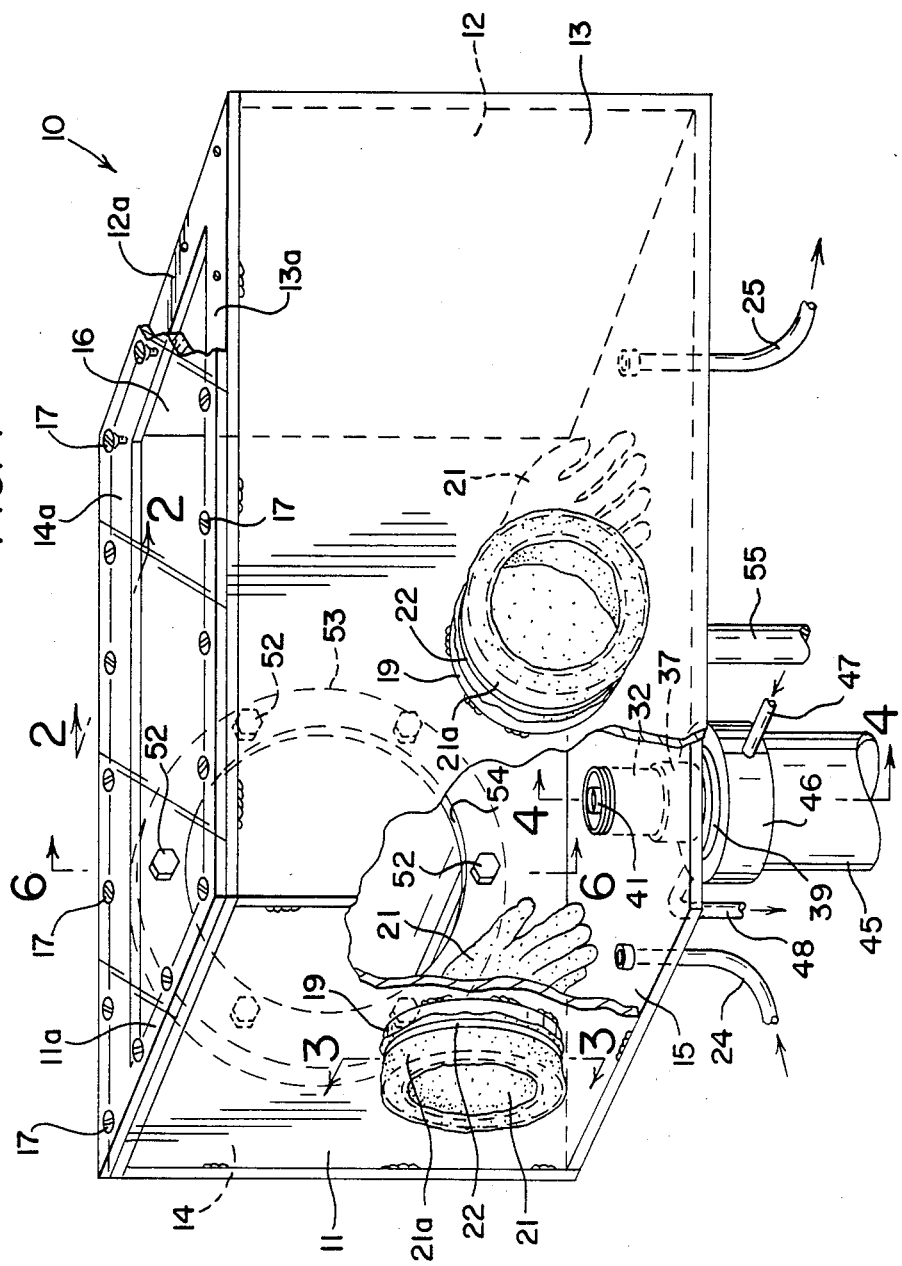
FIG. 1 is an oblique view of a freeze box structure (without glove components) embodying the present invention.
Figure 4:
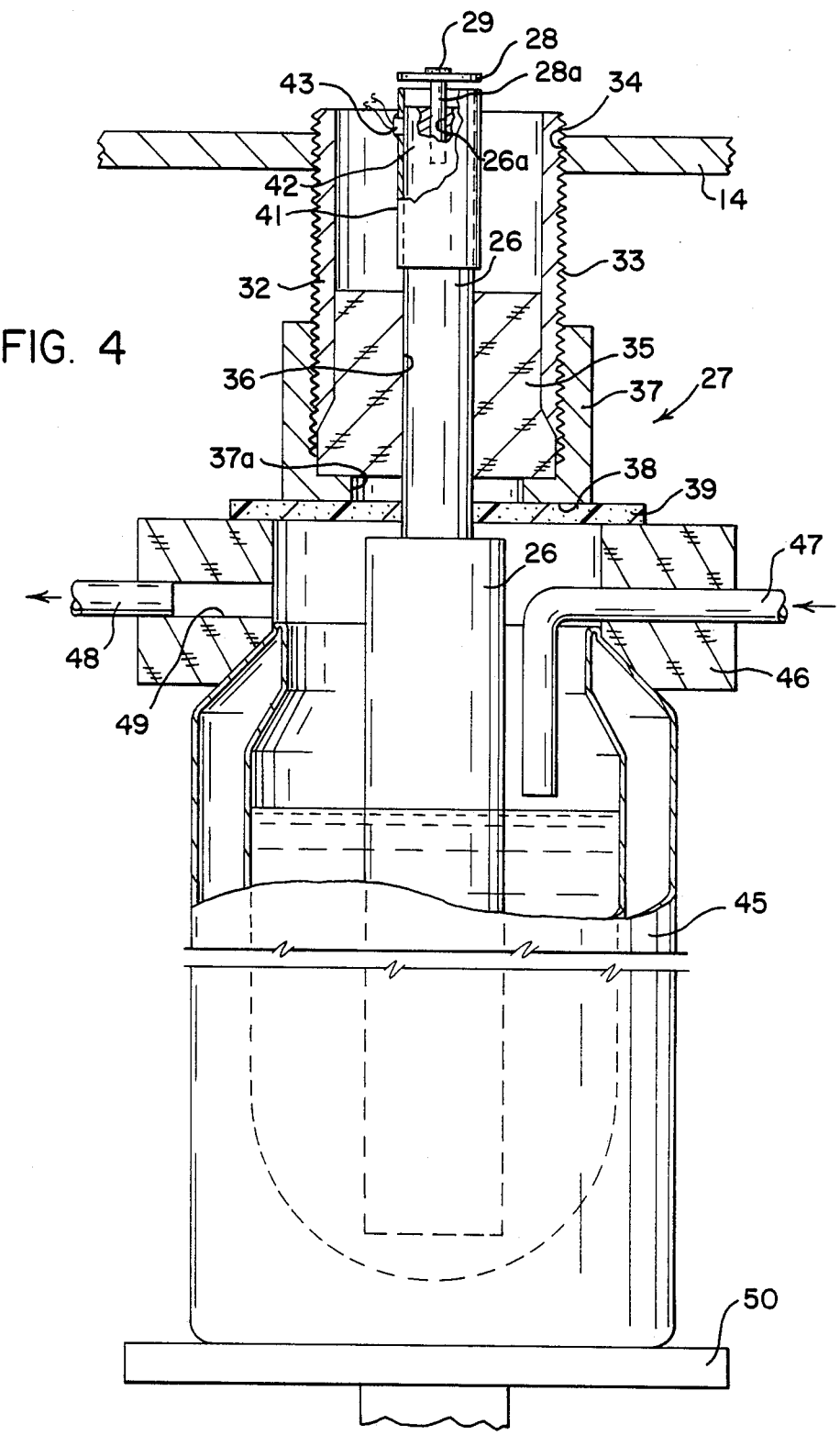
FIG. 4 is a section view along line 4—4 showing the sample supporting freeze rod and feed-through assembly of the freeze box shown in FIG. 1, together with a dewar assembly within which the bottom portion of the freeze rod is confined during operation of the freeze box.

Referring to the drawings, FIG. 1 shows a freeze box 10 comprised of side walls 11,12, front wall 13, back wall 14, floor 15 and cover 16. Side walls 11,12, front wall 13, back wall 14 and floor 15 may be made of any air-impervious material that has sufficient structural strength to withstand the repeated freeze-warm cycles to which freeze box 10 will be subjected in use. Since it is extremely important that freeze box 10 can be hermetically sealed from the outside atmosphere so that no air-leakage can seep into the freeze box 10 when it is in use, all seams and joints of freeze box 10 must be leak-free. Even an incredibly small leak will allow sufficient mositure to enter the freeze box 10 when in operation to cause severe frost build-up within the box at the extremely low temperatures achieved in the freeze box. Aluminum and stainless steel have proven quite satisfactory materials from which to form side walls 11,12, front wall 13, back wall 14 and floor 15, since both aluminum and stainless steel sheet are air-impervious, have adequate structural strength and can be welded to adjacent components of similar composition to form leak-free joints and seams. Five millimeter thick aluminum or stainless steel panels have proven quite satisfactory for use in constructing side walls 11,12, front wall 13, back wall 14 and floor 15. Side walls 11,12, front wall 13 and back wall 14 are provided with inwardly extending flanges 11a, 12a, 13a and 14a which provide a foundation upon which cover 16 rests.

Cover 16, as shown, is formed from a transparent sheet of material (for example, from a glass sheet or from an acrylic plastic sheet) to provide a viewing window into the interior of freeze box 10. Although FIG. 1 shows the entire cover 16 to be transparent, it will be obvious that cover 16 can be formed from a non-transparent sheet material, such as an aluminum or stainless steel panel, with a "viewing port" provided in a convenient location in cover 16. Alternatively, a "viewing port" could be provided in one or more of the vertical walls of the freeze box 10 to permit an operator to see inside the freezer box 10. Cover 16 is attached to flanges 11a, 12a, 13a and 14a by any suitable attaching means, such as by screws 17,17. Cover 16 is hermetically sealed to flanges 11a, 12a, 13a and 14a by O-ring 18 that is seated in groove 19 that extends around the entire periphery formed by flanges 11a, 12a, 13a and 14a. If desired, in addition to O-ring 18, a sealant caulk (such as a butyl rubber sealant) also can be employed between contacting surfaces of cover 16 with flanges 11a, 12a, 13a and 14a to be certain of achieving a hermetical seal.

Side wall 11 and front wall 13 each has a hollow cylindrical glove mounting ring 19,19 hermetically sealed within an opening in the respective wall. Each glove mounting ring 19,19 is provided with a sealing groove 20 that extends around the entire circumference of the outer cylindrical surface 19a of glove mounting ring 19.

A glove 21,21 is associated with each glove mounting ring 19,19 by attaching the cuff portion 21a of glove 21 to the outer cylindrical surface 19a of the glove mounting ring 19 using an elastic sealing cord 22 that extends over the cuff portion 21a of glove 21 and is tightly sealed within sealing groove 20, as shown clearly in FIG. 3, to form a hermetical seal between cuff portion 21a of glove 21 and mounting ring 19. Gloves 21,21 can be extended through their respective glove mounting ring 19 into the interior of freeze box 10 to allow an operator who dons the gloves 21,21 to have access to items contained within freeze box 10 when the freeze box 10 is in use.

Floor 15 of freeze box 10 is provided with a purge inlet tube 24 that is hermetically sealed within an opening within floor 15 and communicates with the interior of freeze box 10, and a purge outlet tube 25 that is hermetically sealed within an opening within floor 15 and communicates with the interior of freeze box 10. As shown in FIG. 1, purge inlet tube 24 is located closely adjacent to side wall 11 while purge outlet tube 25 is located closely adjacent to side wall 12 so that a purging gas (dry nitrogen gas) can be admitted at one end of freeze box 10 and be withdrawn at the opposite end of freeze box 10 to purge the interior of freeze box 10 of moisture when the freeze box 10 is in operation (as will be explained more fully hereinafter).

A freeze rod 26 housed within housing assembly 27 provide means for supporting sample holder 28, a depending shaft 28a of sample holder 28 being positioned in a receiving opening 26a depending from the upper face of freeze rod 26. Housing assembly 27 is comprised of a hollow, generally cylindrical, sleeve 32 that has a threaded outside face 33 to permit the sleeve 32 to be threaded into a threaded opening 34 in floor 14. If necessary, a thread sealant is used to provide a hermetical seal at the location where floor 14 and sleeve 32 are joined. A cork insulating collar 35 is fitted into the bottom of sleeve 32 with freeze rod 26 extending through an opening 36 provided through collar 35, opening 36 being of a cross-section size to promote an air-tight frictional fit between freeze rod 26 and collar 35. An internally-threaded cap 37 is threaded onto the bottom portion of sleeve 32 to retain cork insulating collar 35 securely in place. Cap 37 is provided with an opening 37a through which freeze rod 26 centrally passes. The cross-sectional diameter of opening 37a is larger than the cross-sectional diameter of freeze rod 26 along the zone of freeze rod 26 that passes through opening 37a to provide a sufficient air gap (desirably, a gap of about 6 to 10 mm.) between freeze rod 26 and cap 37 to insure that frost will not bridge from cap 37 to freeze rod 26 during operation of the freeze box 10 and reduce the ability of freeze rod 26 to quickly cool sample 29. An insulating thermal barrier ring 39 through which freeze rod 26 is threaded in friction fit is positioned against the base face 38 of cap 37. The fit between freeze rod 26 and ring 39 normally is sufficiently snug that ring 39 will be held in place against the base face 38 of cap 37 by such frictional fit. However, if desired, an adhesive may be used between base face 38 of cap 37 and ring 39 to insure that ring 39 will remain in place. Freeze rod 26 may be made of any material that conducts cold readily, such as aluminum, stainless steel or copper. A hollow cylindrical frost shield 41 (desirably formed of aluminum or stainless steel) is fitted over the upper tip 42 of freeze rod 26 and is held in place by a friction fit. Frost shield 41 desirably extends above the upper face of freeze rod 26 a distance of at least about 0.125 inch (3.2 mm.) to effectively function to reduce any tendency of frost to form on the upper face of the freeze rod 26. A thermocouple 43 is located in the wall of frost shield 41 to measure the temperature at the upper tip 42 of freeze rod 26.

Cooling of freeze rod 26 is accomplished through use of a dewar bottle 45 fitted with a cork collar 46, the bottom portion of freeze rod 26 being slidably positioned within dewar bottle 45 when the freeze box 10 is being operated. A filling tube 47 extends through collar 46 and communicates with the interior of dewar bottle 45, providing a means for introducing liquid nitrogen into dewar bottle 45. A venting tube 48 is fit into an opening 49 in collar 46 to permit vaporized nitrogen within dewar bottle 45 to escape to the atmosphere. Dewar bottle 45 rests on a base 50 that can be raised or lowered (for example, by a hydraulic lift system) to permit dewar bottle 45 to be raised or lowered relative to freeze rod 26 to change the depth to which freeze rod 26 extends within dewar bottle 45 during operation of freeze box 10.

When freeze box 19 is in use with a surface analysis instrument (for example, a VG Escalab MKII surface analyzer instrument), the freeze box 10 is bolted to the fast entry lock 51 by means of bolts 52,52 that extend through back wall 14 and into mounting flange 53 on fast entry lock 51, as shown best in FIG. 6. An O-ring 56 seated in a groove 57 in the face of mounting flange 53 and extending around the entire periphery of flange 53 insures a hermetical seal between flange 53 and back wall 14 of freeze box 10. An opening 54 through back wall 14 is an alignment with the entrance into fast entry lock 51 when the door (not shown) to fast entry lock 51 is opened so that samples, when properly cooled in freeze box 10, can be moved quickly into the surface analysis instrument to be analyzed.

Freeze box 10 may be supported on a support base 55 extending from floor 15 of freeze box 10 to the ground. Desirably, support base 55 is made adjustable so that a degree of adjustment is available, since with different instruments, when freeze box 10 is bolted to the instrument, the distance from the floor 15 of freeze box 10 to the ground may vary.

To utilize freeze box 10 with a surface analysis instrument, the freeze box 10 is bolted to the sample entry lock 51 of the surface analysis instrument and the support base 55 is adjusted or blocked (if the support base 55 is not adjustable) to provide positive support under the floor 15 of the freeze box 10. Access into freeze box 10 can be gained by removing a glove 21 from the glove mounting ring 19 with which it is associated. One or more samples 29 are prepared and each is placed on a sample holder 28. If a liquid sample is desired to be surface analyzed, a sample holder that has a turned up edge is used to contain the one or two drops of liquid sample which is needed. When the sample is a solid composition at ambient temperature, the composition is formed into a thin sheet (for example, a sheet about 1 or 2 millimeters thick, although thicker samples could be used since it is only the surface of the sample that will be analyzed) and a small sample (desirably a sample about 10 millimeter by 10 millimeters or a disc with a diameter of about 10 millimeters) is cut from the sheet and placed on the sample holder 28, care being taken not to contaminate the surface which is to be analyzed. If a number of different materials are to be analyzed, a number of samples are prepared and placed in the freeze box 10 at one time, a carousel or rack being used to contain the plurality of sample holders with the samples positioned thereon. Conveniently, thermocouple 43 is connected to a temperature readout instrument that is contained within freeze box 10, although the wires of thermocouple 43 can be connected to a temperature readout instrument located outside freeze box 10 provided that a hermetical seal is maintained at the place the wires penetrate the walls of freeze box 10. To assist the operator in transferring a sample holder with sample positioned thereon into the surface analysis instrument after the sample is cooled and for transferring a sample holder with sample positioned thereon from a carousel or rack within freeze box 10 onto the tip 42 of freeze rod 26 when the freeze box 10 is in use, a pair of tweezers or tongs or the like are placed in freeze box 10 before the freeze box 10 is sealed by replacing glove 21. Once the glove 21 has been properly secured to the glove mounting ring 19, the operator should check to be certain that all of the seals are properly in place to provide a hermetically sealed chamber, since even a minute leak will admit sufficient moisture into freeze box 10 during its operation to interfere with the desired analysis of the samples.

The hermetically sealed freeze box 10 then is purged for at least 2-3 hours (desirably for overnight) by introducing nitrogen gas having a very low moisture content (a moisture content below about 0.01 ppm of water being preferred) into freeze box 10 through purge inlet tube 24 and withdrawing the nitrogen gas through purge outlet tube 25 to flush moisture within freeze box 10 from the freeze box 10. The amount of moisture in the nitrogen gas that can be tolerated will vary depending upon the temperature to which a sample is to be cooled. If the sample is to be cooled to only $-20°$ C., nitrogen gas with a moisture content of 0.1 ppm of water could be tolerated without experiencing objectionable frosting. However, if the sample is to be cooled to $-110°$ C. (a temperature often desirable for conducting surface analysis of a material), nitrogen gas with a moisture content of only 0.1 ppm of water is unsatisfactory in that objectionable frosting of the sample occurs. Liquid nitrogen that has been allowed to evaporate in its travel from the liquid nitrogen storage tank to purge inlet tube 24 is a convenient method for obtaining extremely "dry" nitrogen gas. Purging of the interior of freeze box 10 is continued during the entire period the freeze box 10 is in use.

After the initial purge of freeze box 10 for about at least 2-3 hours has been completed (as described above), liquid nitrogen is charged into dewar bottle 45 through fill tube 47. Dewar bottle 45 filled with the liquid nitrogen charge then is raised so that the bottom portion of freeze rod 26 is immersed in the liquid nitrogen. "Cold" will be conducted through freeze rod 26 (actually by removal of heat), to sample holder 28 and, in turn, to sample 29. The temperature to which the sample 29 is cooled will depend upon the depth to which freeze rod 26 is immersed in liquid nitrogen contained in dewar bottle 45, (the more of freeze rod 26 immersed in the liquid nitrogen, the greater the cooling realized). With freeze rod 26 immersed as fully as possible in the liquid nitrogen, a cooling of the sample 29 to a temperature of about $-110°$ usually can be realized in about 10 to 15 minutes. When freeze rod 26 has cooled to within about $10°-20°$ of the desired temperature to which the sample is to be cooled, a sample holder 28 with Sample 29 thereon is lifted onto the tip 42 of freeze rod 26.

Once sample 29 has been cooled to the desired low temperature (usually within 5 to 10 minutes), the operator opens the door to the entry lock of the surface analysis instrument (the entry lock previously having been purged with nitrogen) and transfers the sample holder 28 with cooled sample 29 residing thereon into the surface analysis instrument and to the location within the surface analysis instrument at which the analysis is conducted. The door to the entry lock 51 then is closed.

Before placing another sample to be cooled on the tip 42 of freeze rod 26, dewar bottle 45 is lowered to a position to allow freeze rod 26 to warm (for example, to a temperature of about $-30°$ to $-20°$ C.). Warming the freeze rod 26 will dissipate any minute amounts of frost that may have formed on the freeze rod 26. When the sample 29 that was introduced into the surface analysis instrument has been analyzed, the sample is removed from the surface analysis instrument and the door to the entry lock 51 is closed. Freeze box 10 now is ready for cooling another sample 29 by repeating the steps recited above except that the initial 2-3 hour purge of the interior of freeze box 10 is not necessary. However, once the door to entry lock 51 has been closed following removal of a sample from the surface analysis instrument, a purge of the interior of freeze box 10 with nitrogen gas for from 5 to 10 minutes is recommended.

We claim:

1. A freeze box capable of being hermetically sealed and suitable for use in association with a surface analysis instrument, said freeze box comprising air-impervious side wall panels, a front wall panel, a back wall panel, a floor panel and a cover panel, at least one of said panels containing an air-impervious transparent segment to permit an operator to view into the interior of said freeze box when said freeze box is in operation, said freeze box having at least two outwardly protruding hollow, generally cylindrical glove mounting rings extending through openings in the walls of said freeze box and communicating with the interior of said freeze box at one end and with the ambient atmosphere at the other end, an air-impervious glove with a cuff portion associated with each said glove mounting ring, said cuff portion of said glove being disposed over the exterior outwardly protruding cylindrical surface of the said glove mounting ring with which it is associated, means for clamping said cuff portion of said glove to said exterior cylindrical surface of said glove mounting ring with which it is associated to form a hermetic seal between said cuff portion of said glove and said glove mounting ring, means in said floor panel adjacent on said side wall for introducing an inert purging gas into the interior of said freeze box, means adjacent the other said side wall for allowing the escape of purging gas from the interior of said freeze box, cooling means extending through said floor panel, said cooling means having a freeze rod provided with means for associating a sample to be cooled therewith, said cooling means having means for cooling said freeze rod to temperatures below $-110°$ C., and said freeze box with a surface analysis instrument, said freeze box having an opening to permit a sample cooled in said freeze box to be transferred into the surface analysis instrument.

2. The freeze box of claim 1 wherein said cooling means comprises a dewar bottle filled with liquid nitrogen into which the bottom portion of said freeze rod extends.

3. The freeze box of claim 1 wherein said freeze rod has a hollow cylindrical frost shield over the upper tip of said freeze rod and wherein said frost shield contains a thermocouple for measuring the temperature at the upper tip of said freeze rod.

4. The freeze box of claim 2 wherein said dewar bottle can be raised and lowered relative to said freeze rod.

* * * * *